(12) United States Patent  (10) Patent No.: US 6,716,201 B2
Blanco  (45) Date of Patent: *Apr. 6, 2004

(54) SAFETY TROCAR WITH PROGRESSIVE CUTTING TIP GUARDS AND GAS JET TISSUE DEFLECTOR

(75) Inventor: Ernesto E. Blanco, Belmont, MA (US)

(73) Assignee: Erblan Surgical Inc., Belmont, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/324,050

(22) Filed: Dec. 20, 2002

(65) Prior Publication Data

US 2003/0109894 A1 Jun. 12, 2003

Related U.S. Application Data

(63) Continuation of application No. 09/598,453, filed on Jun. 22, 2000, now Pat. No. 6,497,687.
(60) Provisional application No. 60/140,409, filed on Jun. 22, 1999.

(51) Int. Cl.[7] ................................................. A61M 5/32
(52) U.S. Cl. .............. 604/274; 604/164.01; 604/167.06
(58) Field of Search ................................ 604/264, 272, 604/274, 164.01, 164.02, 164.06, 167.01, 167.03, 167.06

(56) References Cited

U.S. PATENT DOCUMENTS

| 5,364,372 A | 11/1994 | Danks et al. ................. 604/264 |
| 5,387,197 A | 2/1995 | Smith et al. ................. 604/164 |
| 5,399,167 A | 3/1995 | Deniega ....................... 604/164 |
| 5,545,150 A | 8/1996 | Danks et al. ................. 604/256 |
| 5,607,440 A | 3/1997 | Danks et al. ................. 606/185 |
| 5,620,456 A | 4/1997 | Sauer et al. ................. 606/185 |
| 5,624,459 A | 4/1997 | Kortenbach et al. ......... 606/185 |
| 5,669,885 A | 9/1997 | Smith .......................... 606/184 |
| 5,676,682 A | 10/1997 | Yoon ........................... 606/185 |
| 5,690,663 A | 11/1997 | Stephens ..................... 606/185 |
| 5,709,671 A | 1/1998 | Stephens et al. ............. 604/264 |
| 5,776,112 A | 7/1998 | Stephens et al. ............. 604/264 |
| 5,797,943 A | 8/1998 | Danks et al. ................. 606/185 |
| 5,868,773 A | 2/1999 | Danks et al. ................. 606/185 |
| 5,984,941 A | 11/1999 | Wilson et al. ............... 606/185 |
| 5,997,510 A | 12/1999 | Schwemberger ............ 604/164 |
| 6,017,356 A | 1/2000 | Frederick et al. ........... 606/185 |
| 6,063,099 A | 5/2000 | Danks et al. ................. 606/185 |

FOREIGN PATENT DOCUMENTS

| WO | WO 00/54648 | 9/2000 |
| WO | WO 00/78387 | 12/2000 |
| WO | WO 02/28295 | 4/2002 |

OTHER PUBLICATIONS

U.S. patent application Ser. No. 29/144,096, Blanco, filed Jun. 27, 2001.
U.S. patent application Ser. No. 10/092,560, Blanco, filed Mar. 08, 2002.
U.S. patent application Ser. No. 10/313,020, Blanco, filed Dec. 06, 2002.
U.S. patent application Ser. No. 10/324,050, Blanco, filed Dec. 20, 2002.

Primary Examiner—Brian L. Casler
Assistant Examiner—Jeremy Thissell
(74) Attorney, Agent, or Firm—Oblon, Spivak, McClelland, Maier & Neustadt, P.C.

(57) ABSTRACT

A surgical device for endoscopic surgical procedures capable of preventing injuries to internal organs during insertion. The surgical device can include one or more of the following: a multiple system of sharp blade edges, a mechanical tissue protection device that includes a series of thin plastic guards sliding along the sides of the planar knives and having an angle between their edges smaller than that of the cutting knife edges, one or more fixed conical deflectors to expand the cut tissue passage leaving the guards to contact tissue contact only at their tips, an insufflation passage configured to transport fluid into the body cavity during penetration, a locking system for the guards that prevents accidental reuse of the cutting features, and/or an ergonomic design which facilitates handling.

45 Claims, 11 Drawing Sheets

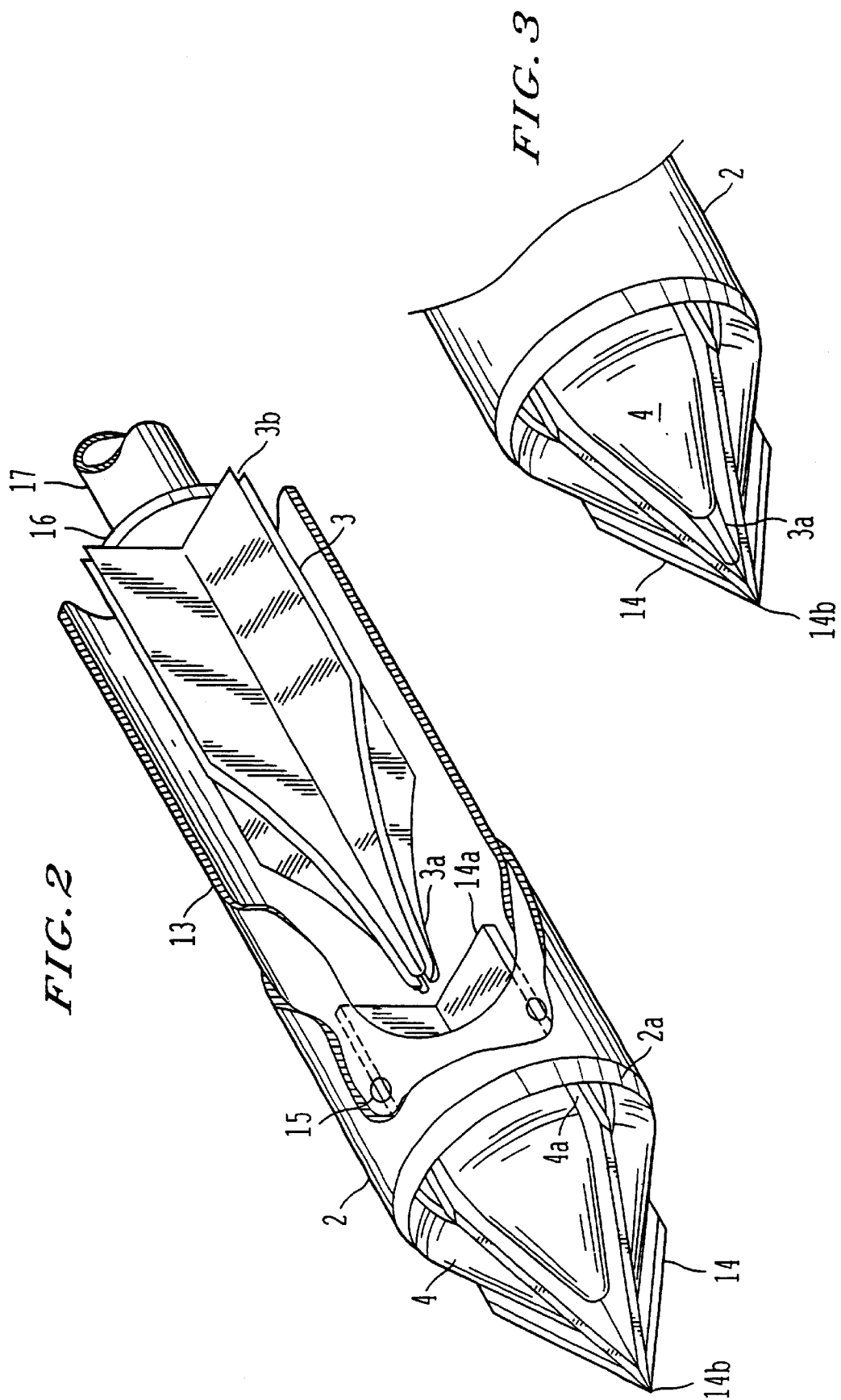

SAFETY TROCAR WITH PROGRESSIVE CUTTING TIP GUARDS AND GAS JET TISSUE DEFLECTOR

BACKGROUND OF THE INVENTION

1. Field of the Invention

The current invention relates to a surgical device and, more specifically, to a surgical device containing one or more design features that allow to the device to be used safely.

2. Discussion of the Background

Most existing trocars used for endoscopic surgical procedures are incapable of truly effective prevention of injuries to internal organs during insertion and manipulation of the trocar. Despite intensive efforts to improve present trocar designs, the results are still dismal. Present procedures frequently injure internal organs, and the resulting wounds are sometimes serious or even fatal. The need for safer trocars is thus imperative, especially given that endoscopic surgical procedures are likely to become more widespread in the future.

Endoscopic or minimally invasive surgery presents an opportunity to improve present surgical procedures and instrumentation comparable only to the revolutionary effect of the introduction of anesthetics in the 19th Century.

Most present day trocars utilize a tip "shield", or cover, for the cutting edges which is usually deployed immediately after penetration of the body cavity has taken place. Such a penetration is fraught with danger of injury to internal organs. However careful a surgeon may be during penetration of the body cavity, the resistance to penetration drops at the last instant prior to damage to the internal organs. This sudden drop in the resistance to penetration is called a "plunge effect" and occurs prior to any safety feature deployment. In some trocars, the penetration is controlled in some fashion, either taking place in small increments or under some form of approximate direct observation, estimate, or monitoring. In all cases, however, the designs result in much of the piercing tip being inserted to a dangerous depth before any protecting devices is deployed. This is perhaps not surprising since, after all, a hole must be made before any protection is deployed.

Since in most cases delicate organs are very close to the inside of the skin layer being pierced, it is advisable to perform the penetration after internal cavities have been filled with carbon dioxide to minimize the danger of accidental injury due to contact with the sharp piercing tip or the cutting edges of the instrument. In most cases, however, the force required or penetration and the elastic nature of the muscular layer cause a severe depression at the surgical portal, therefore bringing the penetrating tip of the instrument closer to the internal organs. In some of those cases, the sudden penetration of the cavity wall and the rapid drop in resistance allow the instrument to be propelled far deeper than desired or is possible to control. Furthermore, friction between the tissue walls and any protective device retards the deployment of the protective device, and an injury almost inevitably occurs.

SUMMARY OF THE INVENTION

Accordingly, one object of this invention is to insure that such events be avoided through a surgical device in which a penetrating tip or cutting edge(s) of the instrument be kept, at all times, sufficiently distant from delicate tissues. Thus, even under dynamic conditions, the probability of injury will be reduced.

A further object of this invention is to provide a surgical device wherein insufflation fluid can be driven into a patient during penetration of the body cavity by the surgical device to drive the internal organs away from the surgical device during penetration. The insufflation fluid of the present invention can either be supplied from an external pressurized reservoir, or compressed (and hence gathered) during penetration of the body cavity by the surgical device.

A further object of the invention is to provide a surgical device that contains one or more cutting edge that provides low frictional forces between the cutting edge and tissue during penetration of the body cavity, thus reducing the force needed to drive the surgical device into the body cavity.

A further object of the invention is to provide a surgical device that includes a protective device that deploys while remaining substantially out of contact with tissue, thus reducing frictional forces between the protective device and ensuring a controlled and advantageous deployment.

A further object of the invention is to provide a surgical device that includes a protective device such as safety guards, wherein the guarding elements have an apex and the angle subscribed at the apex is smaller than the angle subscribed by the blades or cutting elements of the surgical device, thus insuring progressive coverage of the blades or cutting elements during deployment of the protective device.

A further object of this invention is to provide a surgical device with a grip mechanism that allows convenient gripping and twisting of the surgical device during penetration of the body cavity.

A further object of this invention is to provide a surgical device that includes a locking system that prevents accidental reuse of the cutting elements after the tip has been used.

It is therefor desired that this invention, in general, improve surgical safety.

These and other objects of the invention are achieved by a surgical device such as a trocar tissue penetrator including a set of thin planar arrow-pointed cutting blades joined at a cutting point coaxial and within a hollow cylinder penetrator and having the cutting edges converge at a cutting angle at the cutting point. The back outside of the set of cutting blades can be fixed to the inside of the hollow cylinder penetrator with the cutting edges fully protruding. The hollow cylinder can have its front end slotted and each segment pointed in a triangular shape and bent to fit between the blades and having its edges substantially parallel to the edges of the protruding blades but axially recessed behind such edges to act as a tissue expander to prevent contact between inside moving guards and the outside tissue. The slots between the triangularly shaped bent section tissue expanders at the end of the hollow cylinder penetrator can be wide enough to permit the passing between them and the sides of the cutting blades of a guard sheet at least as thick as the blades. A set of elongated axially bent sheet guards can be set to slide freely within the space between the sides of the cutting blades and the triangular bent segments of the hollow cylinder and having their frontal end with a tip angle profile substantially more acute than the adjacent angle of the blade edges and terminating in a very small dull round tip. The angular frontal edges of the bent sheet guards can have shallow angle ends and curving slowly toward the edges so that at no time their angle exceeds that of the adjacent cutting edges. The elongated bent sheet guards inserted between the cutting blades and the triangularly bent segments of the hollow cylinder can be attached at their opposite end to a stem which is urged toward the frontal cutting edges by a coil spring.

The advantageous characteristics of this surgical device include, e.g., the following:

- a multiple system of sharp planar knife edges that practically eliminate lateral friction and provide a reduced resistance to penetration, thereby reducing the penetration "plunge effect" and tissue springback.
- a mechanical tissue protection device that includes a series of thin plastic guards sliding along the sides of the planar knives and, in a preferred embodiment, having an angle between their edges smaller than that of the cutting knife edges. It can then be shown that, with proper contouring of such plastic guard edges, it is possible to provide complete guarding between the cutting edges and the surrounding tissues from the very start of the penetration, and to do so in a truly progressive manner, without jerks or discontinuities. The progressive guarding action that results from the smaller angle between the sides of the guards than the angle between the edges of the cutting blades allows the guards to plunge into the tiny opening made by the cutting tip and instantly surround it, thereby preventing injury to internal organs during the most crucial instant of the trocar insertion. Therefore, guarding action takes place in a truly progressive manner in which, as the cutting blades continue expanding the tiny initial opening, the guards progressively advance keeping the cutting edges constantly covered outside the penetrating region and isolated from internal organs until the penetration is completed and the cannula fully inserted;
- one or more fixed conical deflectors to expand the cut tissue passage leaving the guards to contact tissue only at their tips, thus isolating the guards from friction against the tissue at the sides of the point of penetration. Therefore, as soon as even a minute opening is made at the tip by the cutting blades, the guards instantly plunge into the opening and prevent the blade tips from any contact with internal organs. Thus, using tissue expanders outside the guards prevents friction between the guards and the tissue, which would retard the deployment action. The use of this tissue expander allows the safety device to function without restriction, thereby eliminating one of the major deficiencies of existing trocars. In other words, the dynamic response of the guards is inherently much faster than the rate of penetration of the blades. As a result, cutting edges are never dangerously exposed to, contact with internal organs, however fast the penetration rate may be;
- an insufflation passage configured to transport fluid into the body cavity during penetration. The insufflation passage can be pressurized either using an external reservoir or by compressing gas contained in the passage during penetration. Once an initial penetration of the, epithelium has been made, fluid from the insufflation passage will drive the internal organs away from the cutting edge(s). In the case of an external carbon dioxide gas reservoir, a carbon dioxide gas valve is opened, thereby pressurizing the penetrator tubular body. Under such pressurization, since the front is enclosed by tissue, the cutting tip penetrates the tissues while the gas is prevented from exhausting, but as soon as the most minute opening starts to appear at the tip, the gas expands suddenly into the opening and forcibly deflects delicate internal organs away from the tip of the cutting surface while simultaneously the guard tips are forced through the opening by their spring. The use of a pressurized fluid (or gas) tissue deflector thus creates an organ-free zone in front of the cutting blade tips at the instant of the incipient penetration, even before the guard tips plunge into the opening. It must also be pointed out that a sudden gas expansion can also aid the deployment of the guards since the flow occurs between the cutting blades and the conical expanders, precisely where guards may be located. It could almost be said that the guards are spit out by the fluid flow. This increases the velocity of their deployment and hence the overall safety of the surgical device;
- a locking system for the guards, which is located at the proximal end of the instrument, prevents accidental reuse of the cutting features after the tip has been safely introduced for the first time. The locking system for the trocar guards includes a locking cylinder attached to a locking button supported by a leaf spring and inserted into a socket. The cylinder has a conical tip and a circumferential groove at the bottom and can be depressed by way of the button and engaged by the groove into a U shaped spring that will hold it down permitting it sliding motion until it comes out of the U shaped spring and is ready for locking again on its return to the initial position. If a reset action is desired it is necessary to push hard downward against the locking button and deliberately reset it for another cycle. Since the locking button is located deep within a recess at the proximal section of the handle, it demands some effort to reach and actuate, and thus it is difficult to accidentally reset.
- an ergonomic design which facilitates handling. The proximal hemispherical knob nestles easily into the hollow of the hand while the index and middle fingers control rotation by gripping the side horns, thereby permitting push, pull, rotation, and tilting in a very natural and comfortable manner.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 2 illustrates a partial broken view of the penetrating end of the example trocar with guards removed to behind the tip knives to illustrate a shape of this embodiment more clearly;

FIG. 3 shows the same end of the example trocar with the guards installed but retracted as when penetration of an example embodiment starts, and thus, the knife edges are exposed and ready to start cutting;

DETAILED DESCRIPTION OF THE INVENTION

Figure 1:
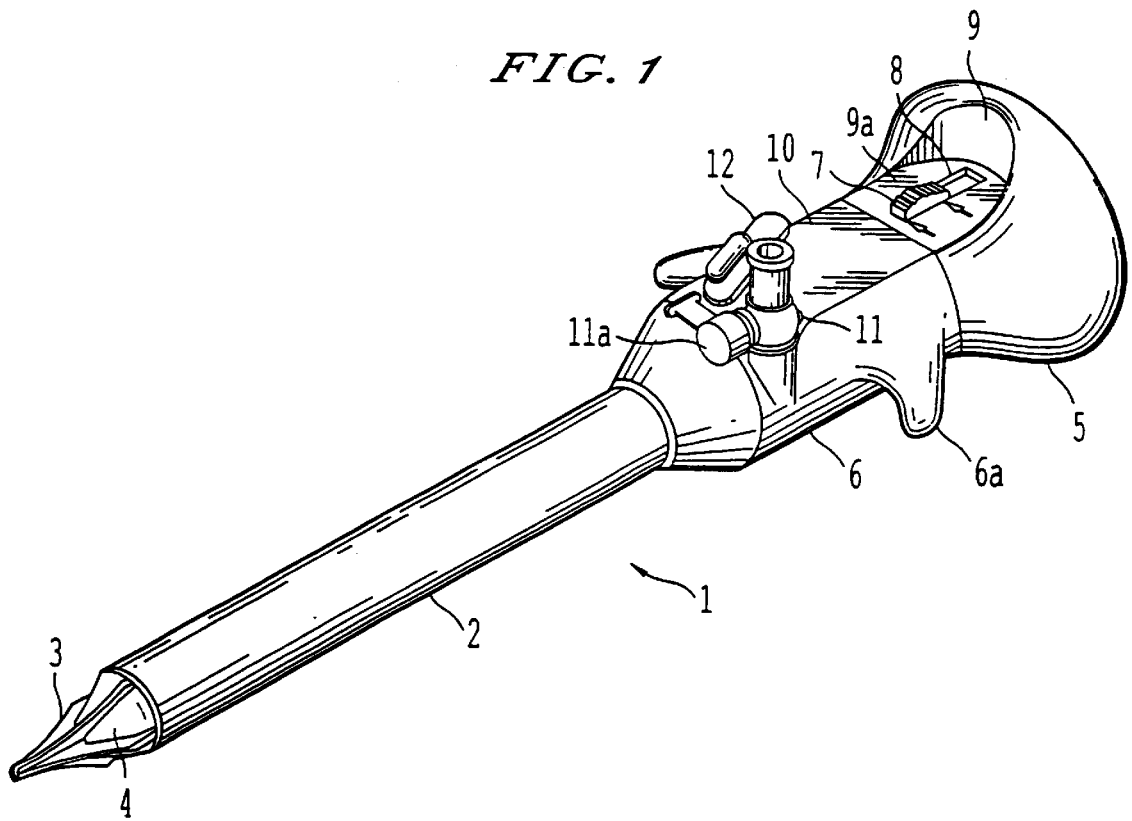
FIG. 1 shows a general view of an example trocar in isometric pictorial form.

Referring now to the drawings, wherein like reference numerals designate identical or corresponding parts throughout the several views, and more particularly to FIG. 1 thereof, wherein a cannula 2 is firmly attached to a distal section of a handle which is formed from two segments, the distal one 6 externally containing gripping horns 6a, insufflation device 11, and flap valve lever 12, and a proximal handle section 5 in the shape of a hemispherical knob to facilitate its pushing with the palm of the hand. This section also contains a depression 9 with a flat bottom 9a, and external mechanisms including a button 7 inserted for sliding into a slot 8 to monitor and control the position of safety guards at the extreme distal end of cannula 2. The safety mechanisms protruding distally from cannula 2 include conical tissue expanders 4, and safety guards 3 intended to cover a set of knives (not visible in this FIG. 1). Those are the externally visible features of this invention.

FIG. 2 shows details at the penetrating distal end of the trocar. A hollow outside cylinder 2 is the cannula which is firmly attached to the distal section of the handle 6 as was described in FIG. 1. Inside of the cannula 2, there is another hollow cylinder 13 which is the penetrator. This is the removable part which is attached to the proximal section of the handle 5, and can be removed after the penetration is completed to allow for the introduction of surgical instruments. The cannula 2 has its distal end beveled as shown by 2a to facilitate its introduction across the tissue opening with minimal resistance. The penetrator hollow cylinder 13 has its distal end formed as a plurality of conical segment expanders 4 which are spaced by slots 4a to allow for the protrusion of pointed flat knives 14 joined at the center of the instrument and resembling thin arrowheads joined at a center. As shown in FIG. 2, the knives are positioned into the penetrator hollow cylinder 13 to a depth shown at 14a. The knife edges outside the slots 4a between the conical segment expanders protrude a substantial distance to insure adequate cutting. The set of knives is assembled into the penetrator cylinder 13 by spot welds 15, or by other similar mechanism. Right behind the crossing of the knife blades can be seen the plastic guard tips 3a. In FIG. 2, the guards are shown as removed from the knives so as to facilitate the understanding of their shapes and relationship to the knives. The subassembly of the guards 3 is part of a support disk 16 which in turn is part of the guards hollow stem 17 connecting them to an actuator spring and locking mechanism at the proximal section of the handle (not shown here). In the real instrument, the guard tips 3a are inserted around the knife blades which fit into the narrow spaces 3b between the guards. The guards are then assembled by being pushed forward until they protrude between the blade sides and the conical expander slots 4a as can be shown in FIG. 3 below. In FIG. 3, the tips of the guards are barely visible because the guards are retracted as when the trocar is first pushed against the skin.

Figure 4:
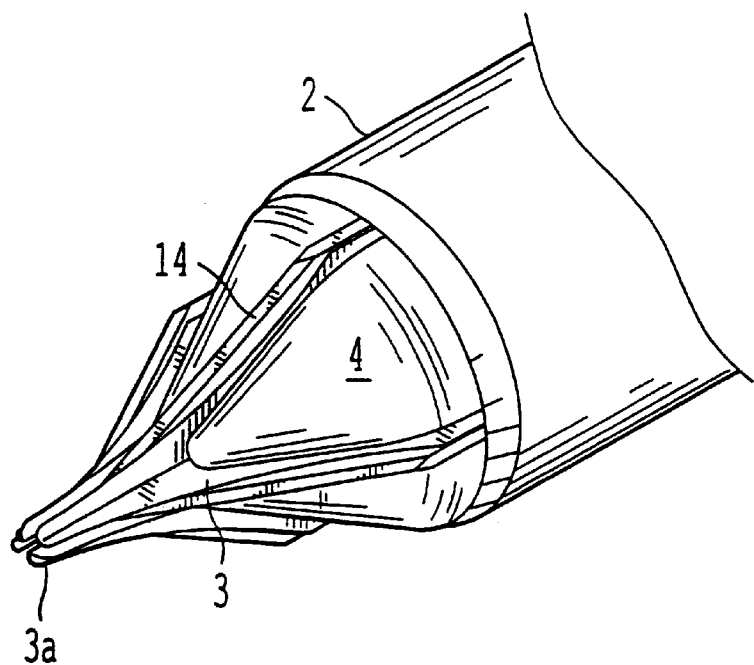
FIG. 4 shows the tip of the guards protruding ahead of the cutting tip as when the tip had just started to pierce the abdominal cavity.
Figure 5:
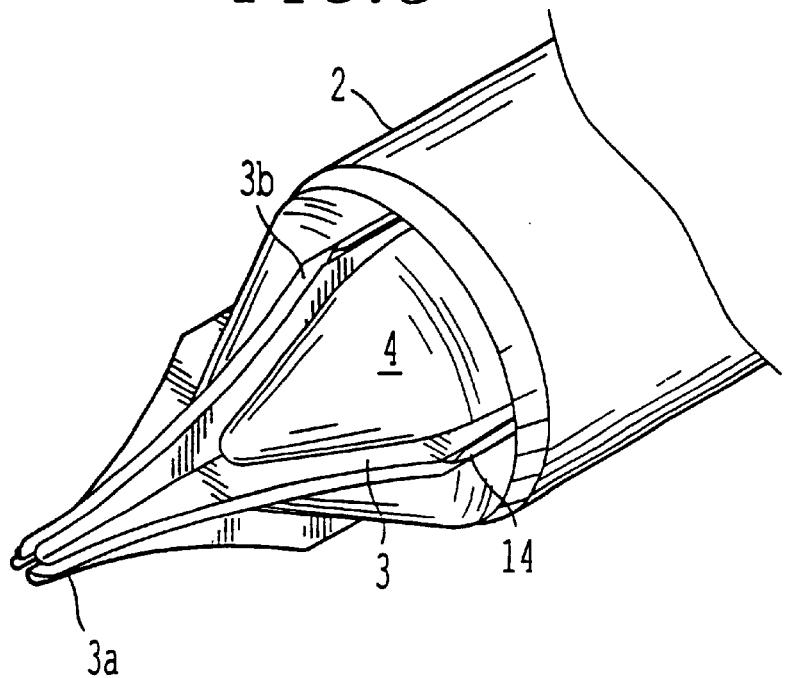
FIG. 5 shows the tip of the example trocar with the guards fully extended and covering the knife edges as when completely inside of the abdominal cavity.

FIG. 4 shows the tips of the guards 3a protruding ahead of the tip of the knives and covering them. A short distance behind the tips of the guards 3a the edges of the knives 14 are exposed and capable of cutting. FIG. 4 shows the configuration of the trocar cutting tip right after initiation of the penetration across the abdominal tissue. At that instant, the guard tiny tips 3a plunge across the start of the opening and quickly cover the sharp cutting point while the exposed knife edges continue cutting inside the skin until the penetration is complete as shown in FIG. 5. FIG. 5 shows how the front end of the example trocar looks after the penetration into the abdominal cavity has been completed. At that time all edges of the cutting knives are covered by the fully extended guards and the whole penetrator assembly can be pulled out with the proximal sector of the handle.

As will be shown later, in one embodiment, at the instant when the first perforation of the abdominal wall was made, a forceful jet of carbon dioxide gas issued across the perforation to deflect away any delicate organs close to the knives tip while simultaneously the guard tips entered the opening to cover the point of the knife edges.

Figure 6:
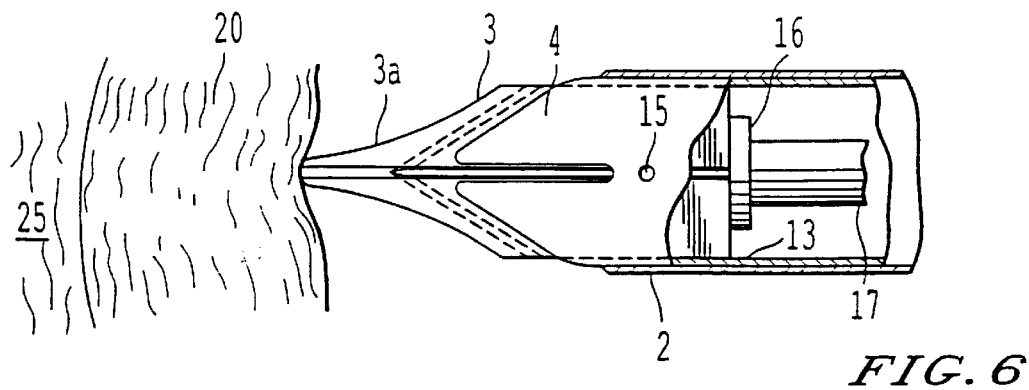
FIG. 6 shows the example trocar tip at the moment it approaches the skin layer, and thus the guard tips are beginning to push against the skin and be retracted into the penetrator.
Figure 11:
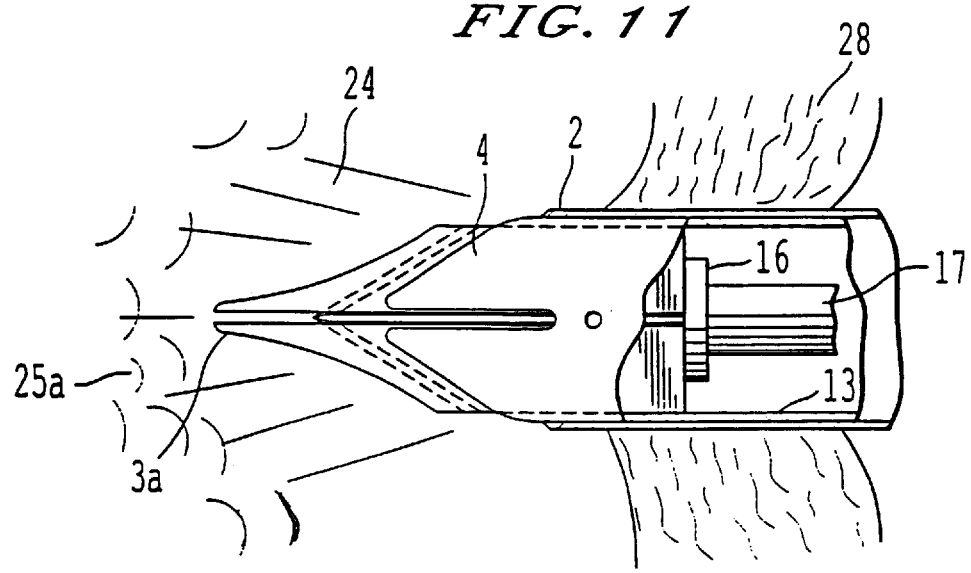
FIG. 11 illustrates the point in an example embodiment when the penetration has been completed. The knife edges are fully covered by the guards and the tissue opening allows for the passage of the cannula and the insufflation continues until completed and the penetrator assembly can be removed.

The operations just described above are a critical part of this invention, therefore they will best be described through the sequence of figures from FIG. 6 through to FIG. 11.

FIG. 6 represents the example trocar guard tips 3a as they begin to contact the skin layer 20. The internal organs are shown at the left side as 25. At this instant, the skin outside layer is deflected under the force of the guard tips which are urged forward by their spring. As the trocar is pushed forward, the guards will be forced into the penetrator 13 and displace the base disk 16 and guard stem 17 toward the right against the force of their spring.

Figure 7:
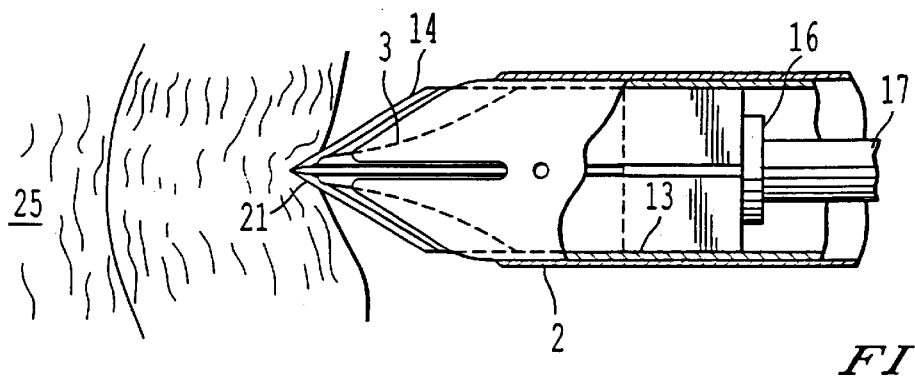
FIG. 7 illustrates the point when, in an example embodiment, the guards are completely pushed into the retracted position and the knife tips start to cut into the tissue.

FIG. 7 shows the guards 3 already completely retracted into the penetrator 13, and the knife edges 14 completely exposed. At that instant, the point of the knives begins to cut and penetrate at 21 into the outside tissue layer. As shown in FIG. 7, the cutting pathway of the cutting tip/knife edge is of a smaller diameter than the inner diameter of the cannula 2 such that the cut made by the blade results in a smaller lumen or bore than that of the cannula. At that time, the carbon dioxide gas is allowed to pressurize the inside of the penetrator 13, and while some gas may escape at first, the tissues around the tip will seal the flow until the cutting tip starts to emerge across the internal abdominal wall.

Figure 8:
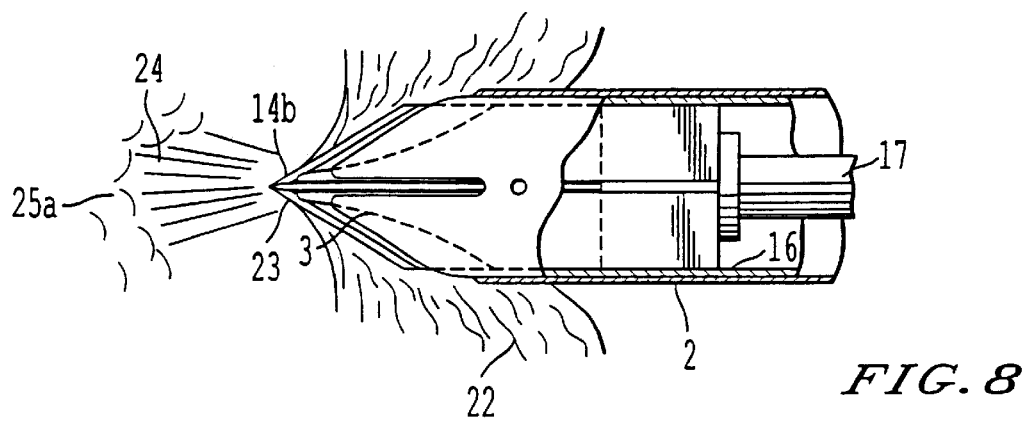
FIG. 8 illustrates the point when, in an example embodiment, the knife tips have completed the passage across the tissue and begin to emerge across the endothelial layer into the abdominal cavity, and thus the tips of the guards begin to push into the incipient opening while a forceful jet of pressurized carbon dioxide gas pushes delicate internal tissues away from the immediate penetration region.

FIG. 8 shows the onset of penetration. At that instant, the cutting tip point 14b has made a very minute perforation 23 and, because of the presence of the guard tips 3a, there is enough space to allow a fluid flow (shown here as a gas jet 24) to issue out and cause the displacement of nearby internal organ tissues 25a, while simultaneously the guard tips 3a expand the opening urged by their spring pushing at 17 and plunge through the perforation effectively covering the cutting tip 14b.

Figure 9:
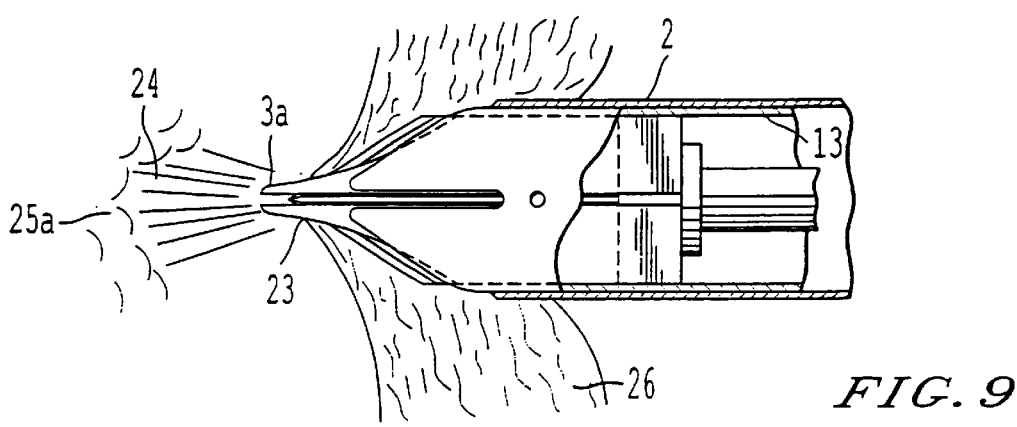
FIG. 9 illustrates the point when, in an example embodiment, the tips of the guards have penetrated the opening and prevent any contact between the knife tips and the surrounding internal tissues while the exposed knife edges behind the opening continue the cutting action, and the pressurized carbon dioxide gas expansion continues to hold delicate tissues away from the cutting region.

FIG. 9 shows the result of the action described above. The gas jet 24 continues issuing and driving internal organs 25a farther away while the guard tips 3a completely enclose the cutting tip 14b. All danger to internal tissues has passed. The extremely quick flow of the gas and the action of the guard tips make the manipulation factors of this trocar the safest to master easily. The force or speed of the penetration action are, within reason, almost immaterial.

Figure 10:
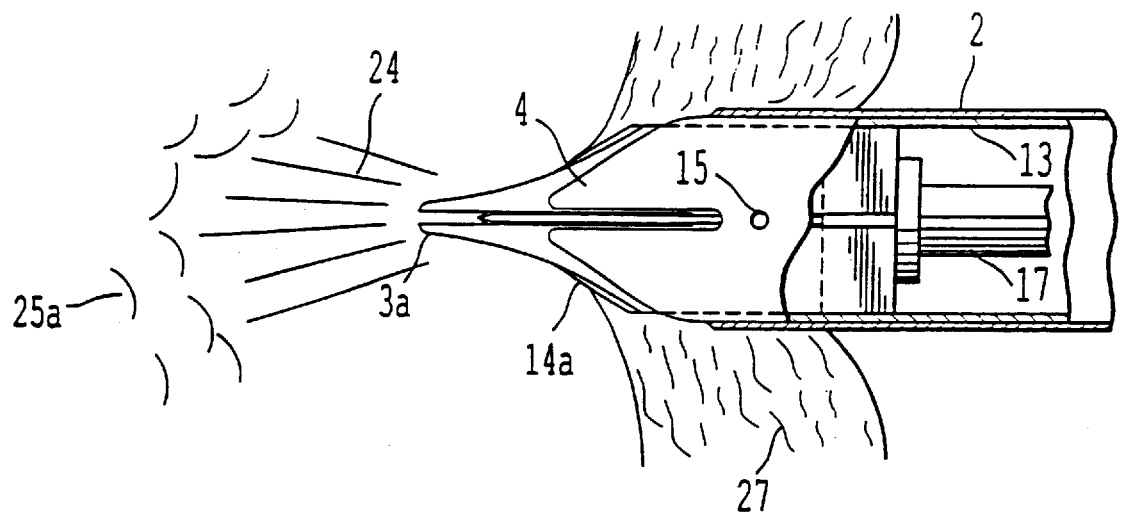
FIG. 10 illustrates, in an example embodiment, the continuing penetration, and thus the guards have penetrated almost completely, while behind them the still-exposed edges continue the cutting action and the passage of gas continues.

FIG. 10 shows the penetration process. The cannula 2 is partly introduced across the tissue 27 and the guard tips 3a continue advancing and protecting the internal tissues from the knife edges while the portions of the edges not yet covered by the guards 14a are seen cutting the remainder of the opening ahead of the cannula, and the tissue expanders 4 facilitate penetration by protecting the guards from tissue friction. At this point of the penetration the flow of carbon dioxide gas 24 is fairly unimpeded and performs the insufflation stage of the process, driving internal organs 25a farther away from the trocar portal.

FIG. 11 shows the trocar after full insertion and in the last stage of insufflation. The knife edges are now fully covered by the guards, and the cannula 2 is seen fully inserted across the tissue. The insufflation continues until completed and then the penetrator 13 is removed to allow the insertion of surgical instruments across the cannula.

Having described in sequential detail the insertion, guarding, and insufflation operations, and the mechanical parts that perform them it remains to describe the additional way by which all that is accomplished. The mechanisms that allow this are located in the handle of the instrument.

Figure 12:
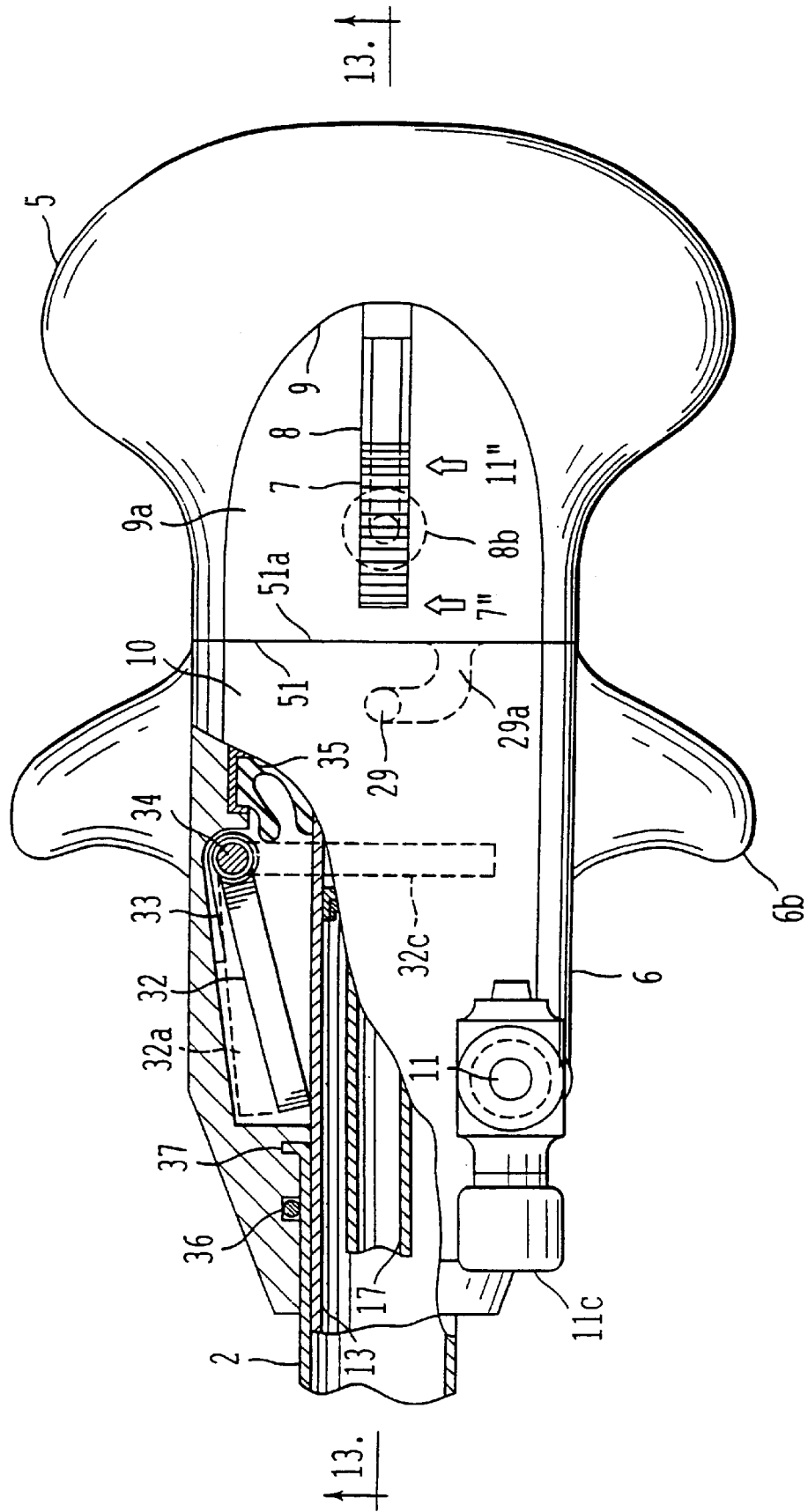
FIG. 12 shows the top view of an example trocar handle with a portion broken away to show some internal details.

FIG. 12 is a top view of the trocar showing some of the external parts as well as a partial broken view of some interior parts. The body of the handle is made out of plastic and has two main segments. The proximal segment 5 is designated to fit into the palm of the hand and has a proximal end of hemispherical shape with a depression of arcuate profile 9 at the top terminating at a flat surface 9a where the guard stem controls are located. Those controls are recessed into the flat depression 9a to prevent unwanted actuation, and include a double slot with vertical slots 8 and 8a into which is inserted a button 7 and its rectangular guiding shank 7a. The button 7 is capable of vertical and horizontal movement, the latter movement being limited between arrows 7" and 11" as will be described later. The proximal segment 5 is assembled as an integral part of the penetrator system. Its distal end 51 forms the interface between the two segments of the handle.

The distal segment 6 of the handle has two lateral protruding horns 6b to facilitate its manipulation during penetration and orientation. The two handle segments 5 and 6 are locked together during usage by way of a bayonet stud 29 and slot 29a. During insertion the stud 29 on part 5 is aligned with the slot 29a on part 6, pushed, and turned clockwise, until the stud locks the two segments firmly, the knob on 5 and the horns 6b provide a good grasp for that operation. The slot 29a has a slant at the transversal direction running slightly away from the interface 51 so as to insure that the turning-locking motion will assure a firm and stable connection. This will be discussed further in reference to FIG. 14.

The partial broken section at the top left of the distal segment 6 is intended to show the operation of the flap valve 32, which acts as a check valve in the illustrated embodiment. The valve has a shaft 34 pivoted between the upper 6 and lower 6a portions of the handle and is urged to rotate counterclockwise by a torsional spring 33 located around the shaft 34. The shaft of the flap valve is firmly attached to the valve and can be rotated from outside the body segment 6 as will be shown later on FIG. 14. An external lock allows the valve to remain open during desufflation if turned hard to its stop position 32a shown in dotted lines. As shown in the embodiment illustrated in FIG. 12, the valve has been opened by the insertion of the penetrator 13. In other cases, the valve could be opened for surgical or visualization instruments. When left to itself, the valve will turn counterclockwise and snap shut against the face of seal 35 which serves as face seal for the valve and lip seal for the penetrator 13. The left end of FIG. 12 shows how the cannula 2 is attached to the handle segment 6 by way of a flange 37, and prevented from leaking by an "O" ring 36. In the same FIG. 12 is shown how the carbon dioxide gas spigot manual valve 11 is mounted at one side of the top of segment 6.

Figure 13:
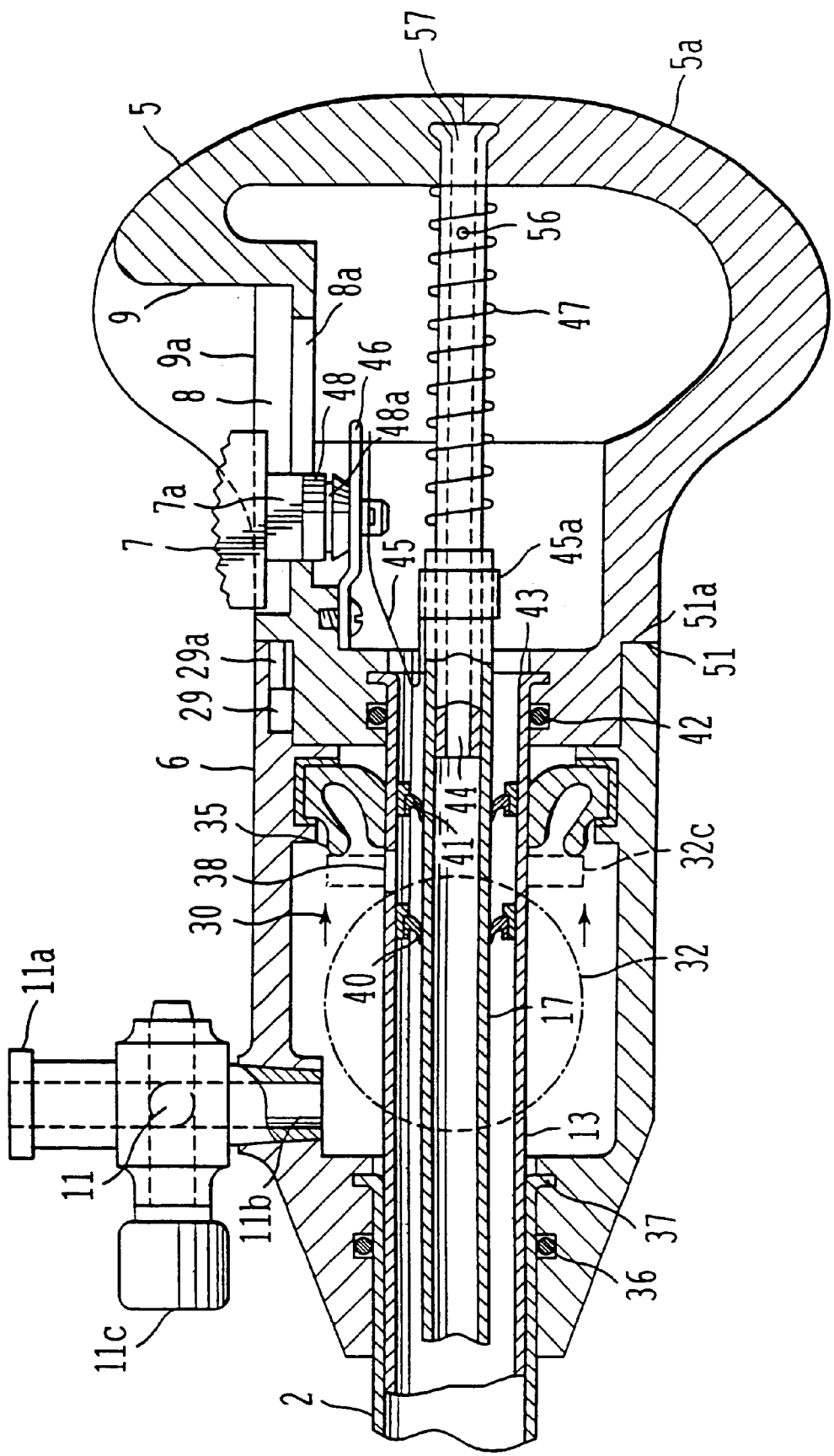
FIG. 13 illustrates a longitudinal section along a vertical plane "A—A" to exhibit most of the internal details of an example trocar handle.

FIG. 13 is a longitudinal vertical cross section along a plane "A—A" to show the internal details of the handle. As can be noticed, the two segments of the handle include a top and a bottom part split along a horizontal plane for fabrication, one becoming 5 and 5a, and the other 6 and 6a, and after each segment has been fitted with the internal parts at assembly the two halves of each segment are permanently bonded together. Each of the two segments is assembled separately since they must be detached and attached during usage. The penetrator segment is only used to make the entry portal, but it must be emphasized that it is such step that involves the greatest risk.

The distal segment made of parts 6 and 6a houses the cannula 2 and all the gas infusion and valving. The connection of the cannula to the segment part 6 was described before. FIG. 13 shows the gas connector or layer 11a to which the gas line is affixed. The valve system is bonded via a conical stem 11b into a boss on plane 10 so the incoming gas flows in the direction of arrow 30 and pressurizes the space between the inlet and the seal 35 from where it can enter the openings 38 around the penetrator 13 walls and fill the space between lip seals 40 and 41. Since the lip seals are oriented toward the front the pressure will open lip seal 40 but not lip seal 41 and the gas will fill and pressurize the entire space along the penetrator 13, not being able to escape when the trocar tip has been inserted into the tissue, however, as soon as the smallest opening is made by the point of the blades the gas will escape as a jet and deflect the surrounding internal organs away from the entry portal. Lip seal 40 is intended to prevent back flow from the penetrator in case of accidental opening or leakage across the gas valve during a procedure. In such a case, the pressurized volume of gas within the penetrator 13 will suffice to insure the safe deflection of nearby tissues even before the tips of the guards 3a plunge into the opening. The guards stem 17 is completely sealed at the front by disk 16 and thereby its interior can be at atmospheric pressure, however, since it must slide back and forth with the guards it must also be supported at the proximal end and must be guided over a stationary hollow steel stud 44 inserted into it to a minimal depth of four diameters. The proximal end of stud 44 is flared to provide fixation between parts 5 and 5a of the proximal hemispherical knob. A hole 56 on the hollow stud 44 serves to provide air passage in and out of the stud when the guards stem moves back and forth acting as a piston pump. The hole 56 should pass through the stud and be of a diameter such as not to impede flow and dampen the sliding action of the guards' stem. Compression coil spring 47 mounted around stud 44 serves to provide the required force to urge the guards stem in the distal direction. The proximal end of the penetrator outside cylinder 13 is flared at 43 for fixation onto the proximal handle segment parts 5 and 5a. It is also sealed at the front by an "O" ring 42 to insure that no leakage of gas would occur even if seal 35 should leak: flared tubular assemblies like 43 are not reliable seals.

Figure 16:
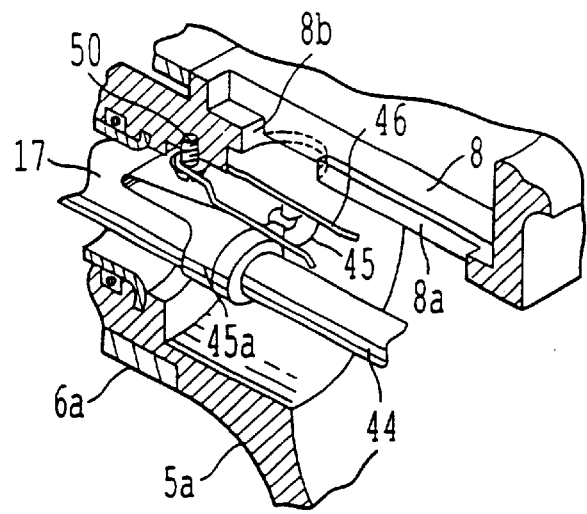
FIG. 16 illustrates a partial isometric view of the example locking mechanism for the guards stem showing some of the elements within the proximal section of the handle as in Section "A—A" on FIG. 13.
Figure 17:
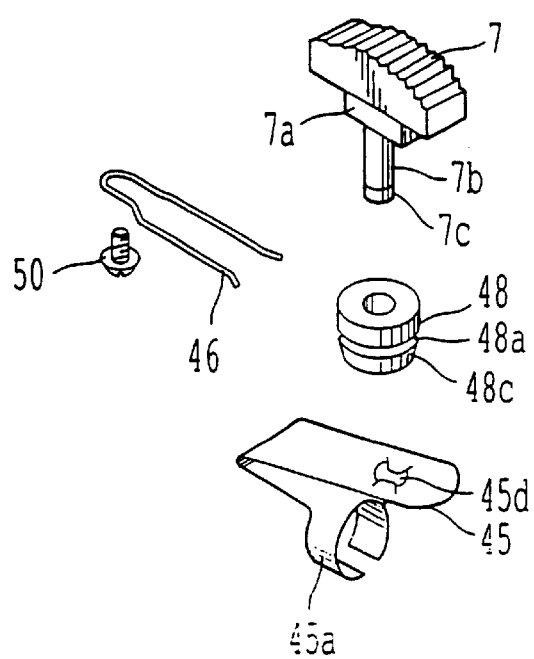
FIG. 17 illustrates an exploded view of some of the example elements of the guards stem locking mechanism in an example spatial relationship.
Figure 18:
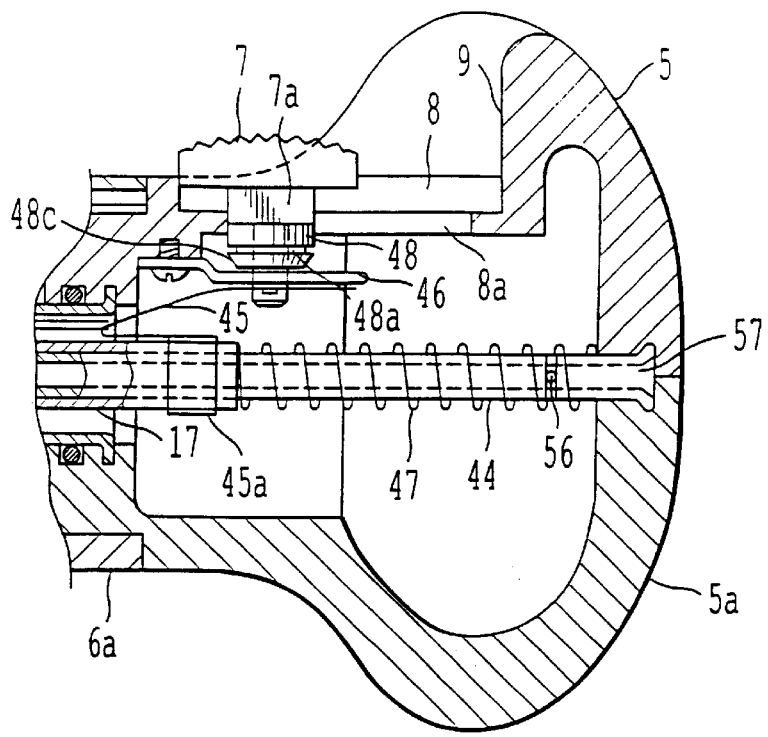
FIG. 18 illustrates an example locking mechanism in a locked position.

The proximal handle segment formed by 5 and 5a is attached to the penetrator 13 and contains all its functional and control elements. The guards stem 17 has at its proximal end a shallow cylindrical depression into which a thin ring 45a which is part of leaf spring 45 is affixed. The exact configuration of the locking system to which the spring 45 belongs can be seen in FIGS. 16 and 17, and its function in the sequence of FIGS. 18 through 22. FIG. 17 is an exploded view of some of the elements of the locking system in their proper relationship. At assembly, the button 7 is inserted across slot 8 on the top surface 9a on FIG. 13 and the locking cylinder 48, which has a circumferential groove 48a and a conical end 48c is pushed up along the stem 7b against the bottom of the rectangular guide 7a thereby assembling button 7 into the slot 8a. As the assembly continues the lower tip of stem 7b is pushed hard against the punched hole 45d of the leaf spring until groove 7c is gripped by the lateral tabs at 45d and the assembly of the button is complete. If now the open hollow cylinder 45a is snapped onto the surface depression at the proximal end of stem 17, the button 7 becomes axially fixed to stem 17 and will follow its back and forth motion in response to coil spring 47 and the forces at the tip of the guards. FIG. 16 shows the assembly of the U spring 46 to the lower inside of 5 by the use of screw 50. FIG. 16 does not show button 7 for the sake of clarity, but it shows flat spring 45 pushing up against the bottom of the U spring 46. If the assembly of the button 7 and the locking cylinder 48 was shown there, it would be evident that the button would be pushed upwards and the locking cylinder 48 would be forcibly inserted into the round socket 8b, thereby preventing any motion of the flat spring 45 and the guards stem 17 attached to it by ring 45a. That is the situation depicted on FIG. 13.

Figure 19:
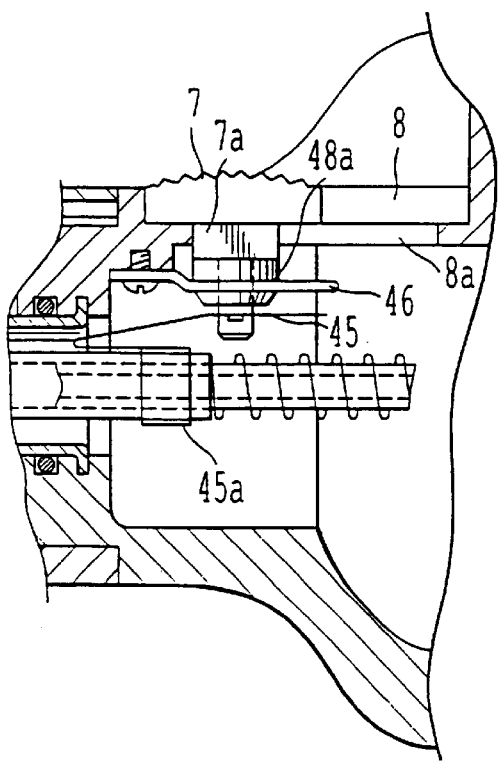
FIG. 19 illustrates an example locking mechanism having been unlocked and ready for the start of penetration.
Figure 20:
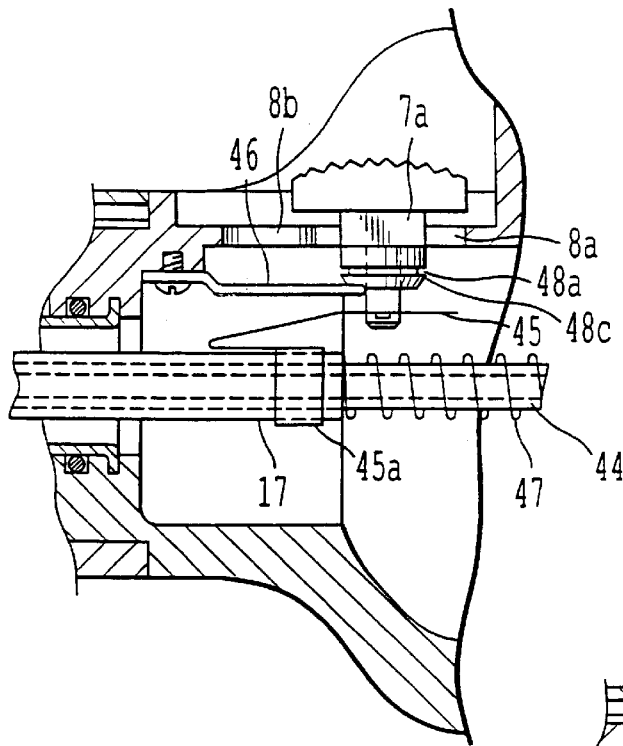
FIG. 20 illustrates how pushing the guards against the skin has forced their stem towards the right.
Figure 21:
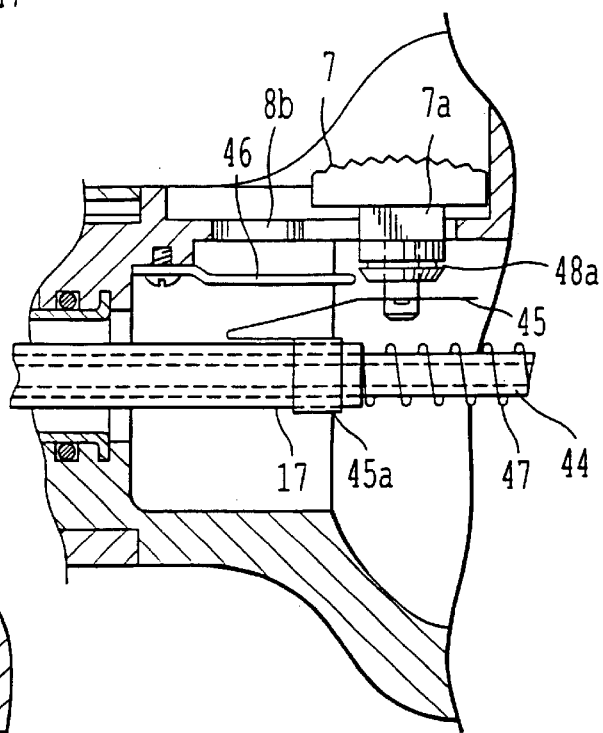
FIG. 21 illustrates a position of the stem where the guards are completely retracted and the knife edges fully exposed for cutting.
Figure 22:
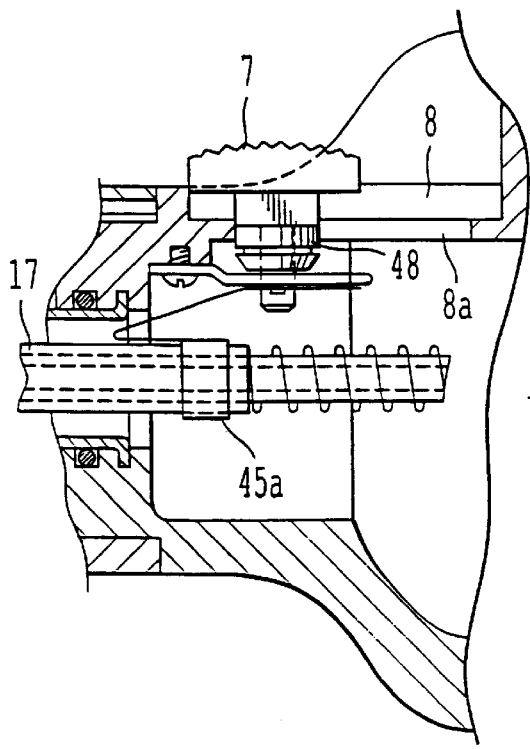
FIG. 22 illustrates a position of the locking mechanism after the full release of the guards into the abdominal cavity and the locking of their stem back to its initial position shown in FIG. 18.

FIGS. 18 through 22 describe an operation of an example locking system in detail, as follows. In the position illustrated in FIG. 18 the system is locked: the guards stem and the guards cannot move at all since the cylinder 48 is inserted into the round socket 8b. FIG. 19 shows what happens when button 7 is pushed down. When that is done the conical end 48c of cylinder 48 opens the U spring 46 and the spring then snaps close into the groove 48a thereby disengaging the locking cylinder from the round socket 8b. The system is then unlocked. The trocar is said to be "armed", and able to permit the motion of the guards backwards, exposing the cutting blades for penetration of the skin. That is the position depicted on FIG. 6. The following discussion is directed to the embodiment shown in FIG. 20. The penetrating force against the skin pushes on the guards and the guards stem 17, and the connecting flat spring 45 moves the button 7 proximally. The rectangular slide section 7a enters the space between guides 8a, and soon afterwards, the locking cylinder groove 48a disengages from the open end of the U spring 46, and the spring 45 pushing upwards against the stem groove 7c forces the top of the locking cylinder to snap against the underside of the groove 8a. In that position, the locking cylinder 48 is free to continue sliding along the underside of groove 8a as shown in FIG. 21 until the initial penetration is made and the force of the coil spring 47 urges the guards stem 17 and the flat spring 45 to return the button 7 to its initial position, at which time the locking cylinder will pass freely over the U spring 46 and snap back into the round socket 8b locking the system into the "safe position" where the guards cannot move accidentally. FIG. 22 shows the completion of the cycle back to the initial configuration of FIG. 18.

A quick review of the provided example locking system from the user viewpoint reveals that the operations include "arming" the trocar by pushing down on the button at the top of the handle at position 7' shown in FIG. 12, until it "snaps" down; then pushing the trocar against the skin and watching or listening to the position of the button as it slides towards 7' and then "snaps" to its initial position 7'. That will be the indication of having completed the penetration. If, for any reason, button 7 were pushed down accidentally, it could be reset to the "safe" condition by merely moving it in the direction to 7' and then releasing it. It should then get snap-locked at a high level in position 7', and could not be moved without first pushing it down.

Figure 14:
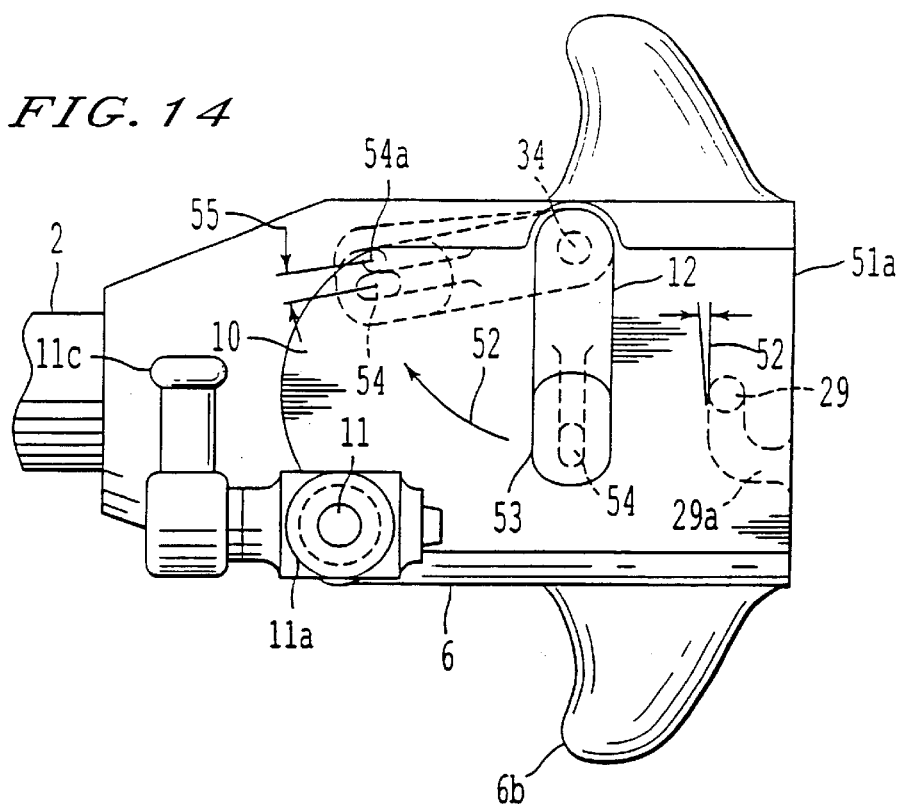
FIG. 14 illustrates a top view of the distal section of an example handle with the grasping horns to facilitate manipulation.
Figure 15:
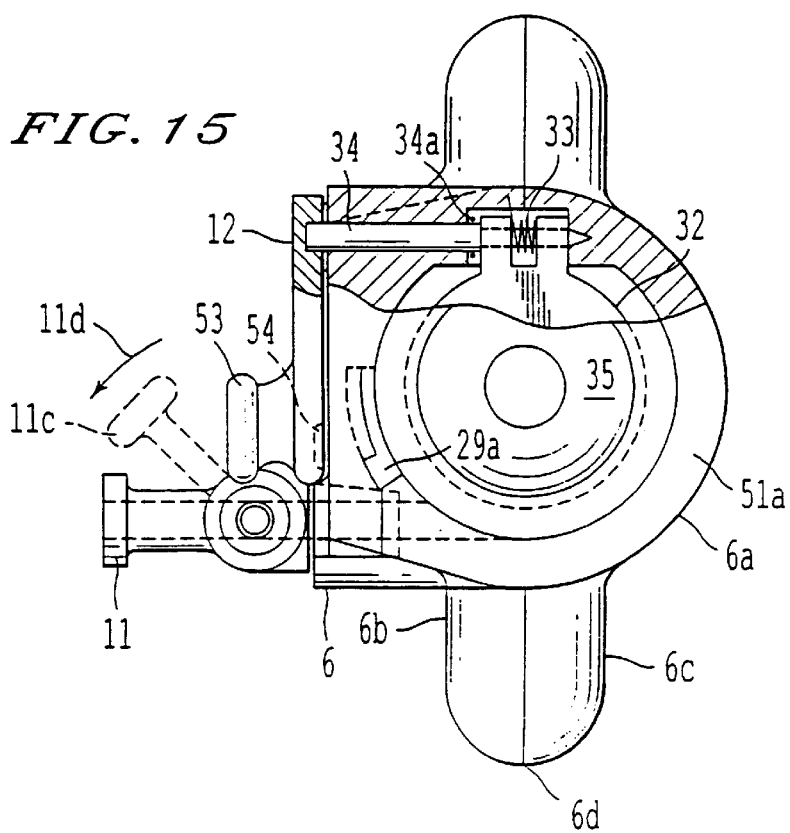
FIG. 15 illustrates an end view of the distal section of an example handle as seen from the right showing also a partial broken section detail of the flap valve pivot and lever.

The details of operation of the example flap valve, its design, and locking for deflation are seen in FIGS. 14 and 15. FIG. 14 shows the top view of the handle distal segment, previously presented in FIG. 12 as a partial broken section to show the interior details. FIG. 14, however, is intended to show the external operative controls on this segment of the handle in the interest of the user. The flap valve lever 12 is shown in the closed position as it should be when the penetrator is removed. The lever is attached to a shaft 34 whose opposite end is attached to the flap 32 as seen in FIG. 15. The insertion of the internal trocar elements is performed when the top 6 and bottom 6a of each handle segment are separated prior to their being bonded along plane 6d.

FIG. 15, as explained before, is the end view of the example embodiment previously illustrated in FIG. 14 as seen from the right side. That is how the distal segment of the handle will appear when the proximal segment is removed. The flap valve external lever knob 53 is provided with a small depression 54 at its bottom to allow it to be held open when the depression is forcibly made to engage a small knob 54a protruding from the flat surface 10 after the lever has been turned in the direction of arrow 52. That is the desufflation position of the valve which allows the surgeon to use both hands to massage the insufflated region and expel the gas retained by the patient at the end of the procedure. The arc of rotation needed for the lever to engage the protruding knob 54a is labeled as 55. This locking position is not reached by the lever when the valve is opened by the insertion of the penetrator. The locking of the valve has to be done by the forceful and deliberate action of the surgeon. The small angle 52 shown at the bayonet locking stud 29 refers to the desirable slant for the groove 29 so as to insure that the locking force increases sufficiently to prevent accidental loosening between the proximal and the distal segments of the handle. The elasticity of the locking elements determines the exact angle to be used, which should be somewhere between 2 and 5 degrees to account for tolerance errors. The infusion valve 11, its lever 11c, and its lever connector 11a are shown on FIG. 14. In FIG. 15, the opening of the valve is indicated by arrow 11d. FIG. 15 also shows a broken section of the valve shaft 34, its top "O" ring seal 34a, and its torsion spring 33 inserted into a slot in the operating bracket of valve 32. In the same FIG. 15, the seal 35 is seen, as well as the front surface 51a of the distal handle segment, which contacts the mating surface 51 of the proximal segment.

Obviously, numerous modifications and variations of the present invention are possible in light of the above teachings. It is therefore understood that within the scope of the appended claims, the invention may be practiced otherwise than as specifically described herein. In particular, it is understood that the present invention may be practiced by adoption of aspects of the present invention without adoption of the invention as a whole.

What is claimed is:

1. A surgical device, comprising:
    a penetrator having a main axis and being attachable to a handle for being gripped;
    a cutting blade located at a distal end of said penetrator and housing a cutting tip; and
    a guard positioned within said penetrator, said guard being movable with respect to said blade, said guard being configured for selectively exposing said cutting blade wherein said guard has an apex such that an angle subscribed at the apex of the guard is smaller than an angle subscribed by said blade tip for progressively covering said blade during deployment of the penetrator.

2. The surgical device according to claim 1, which comprises a tissue expander at a distal end of the penetrator for expanding a tissue cut by said cutting tip.

3. The surgical device according to claim 1, which comprises an insufflation passageway configured to discharge a pressurized fluid upon said cutting blade penetrating a body tissue and to communicate said pressurized fluid to the body tissue upon said cutting tip substantially penetrating the body tissue.

4. The surgical device according to claim 3, wherein said surgical device further comprises:
    an external reservoir for supplying said insufflation passageway with said pressurized fluid.

5. The surgical device according to claim 4, wherein said surgical device further comprises:
    a check valve positioned between said insufflation passageway and an exterior of the surgical device, said check valve being configured to prevent leakage from said insufflation passageway.

6. The surgical device according to claim 5, which comprises:
    a locking system for locking and unlocking the guard in position so as to selectably expose said cutting blade during cutting of the tissue and to progressively cover the cutting tip of the cutting blade after a most distal point of the cutting tip has substantially passed through a layer of the tissue.

7. The surgical device according to claim 3, wherein said insufflation passageway is configured to be pressurized during an insertion of said cutting tip into the body tissue.

8. The surgical device according to claim 7, which comprises a seal which is concentrically positioned with said penetrator, said seal being positioned in said handle and being sealingly engageable with said flap valve.

9. The surgical device according to claim 1, wherein said pressurized fluid comprises a gas and wherein said cutting blade has one of a substantially dull tip and a substantially rounded tip.

10. The surgical device according to claim 1, wherein:
    said cutting blade includes at least one blade having one of a substantially rounded tip and a substantially dull tip.

11. A surgical device according to claim 1, wherein said penetrator is removably insertable into the handle.

12. A surgical device according to claim 11, which comprises:
    a locking system for locking and unlocking the guard in position so as to selectably expose said cutting blade during cutting of the tissue and to progressively cover the end of the cutting blade after a most distal point of the cutting blade has substantially passed through a layer of the tissue.

13. A surgical device, comprising:
    a penetrator having a main axis and being attachable to a said handle for being gripped;
    a cutting blade located at a distal end of said penetrator and having a cutting tip;
    an insufflation passageway configured to discharge a pressurized fluid while said cutting tip is inside a body tissue and to communicate said pressurized fluid across said body tissue when said cutting tip substantially penetrates said body tissue;
    an external reservoir for supplying said insufflation passageway with said pressurized fluid;
    a check valve positioned between said insufflation passageway and an exterior of the device, said check valve being configured to prevent leakage from said insufflation passageway, wherein said check valve comprises a flap valve openable by said penetrator upon insertion of said penetrator into said handle, and
    a guard movable with respect to said cutting blade wherein said guard has an apex such that an angle subscribed in the apex of the guard is smaller than an angle subscribed by said blade for progressively covering said blade during deployment of the penetrator.

14. The surgical device according to claim 13, wherein said insufflation passageway passes through said penetrator.

15. The surgical device according to claim 14, wherein said cutting blade has one of a substantially dull cutting tip and a substantially rounded cutting tip.

16. A surgical device according to claim 13, wherein said penetrator is removably insertable into the handle.

17. A surgical device according to claim 16, which comprises:
a locking system for locking and unlocking the guard in position so as to selectably expose said cutting blade during cutting of the tissue and to progressively cover the end of the cutting blade after a most distal point of the cutting blade has substantially passed through a layer of the tissue.

18. A surgical device according to claim 13, which comprises:
a locking system for locking and unlocking the guard in position so as to selectably expose said cutting blade during cutting of the tissue and to progressively cover the cutting tip of the cutting blade after a most distal point of the cutting tip has substantially passed through a layer of the tissue.

19. A surgical device, comprising:
a penetrator having a main axis and being attachable to a handle for being gripped;
a cutting blade located at a distal end of said penetrator;
a guard movable with respect to said cutting blade, said cutting blade having a cutting tip and being configured to expose said cutting tip while said cutting tip is beginning to cut a tissue layer and while said cutting tip is in said tissue layer, and to progressively cover the end of said cutting tip immediately after a most distal point of said cutting tip has substantially passed through said tissue layer;
said guard having a safety guard edge smaller than a blade edge angle defined by said cutting blade.

20. The surgical device of claim 19, further comprising:
a spring configured to allow translation of said guard responsive to a force generated during a driving of said cutting tip into and through said tissue layer.

21. The surgical device according to claim 20, wherein said cutting tip comprises one of a substantially dull cutting tip and a substantially rounded cutting tip.

22. The surgical device of claim 19, which comprises a tissue expander located proximal to said cutting tip.

23. The surgical device according of claim 19, which comprises a penetration monitor mounted on the handle for indicating a position of said guard relative to said cutting tip.

24. The surgical device according to claims 1, 14, or 23, wherein said cutting blade comprises:
a substantially planar blade having a first blade edge, said first blade edge being attached to a distal end of said penetrator and oriented substantially parallel to a main axis of said penetrator and being configured to produce an opening in a body tissue for an insertion of a surgical cannula.

25. The surgical device according to claim 24, wherein said cutting blade further comprises:
a second blade having a second blade edge, wherein:
said second blade is attached to a distal end of said penetrator and oriented substantially parallel to said main axis of said penetrator; and
said second blade edge being configured to intersect said first blade edge at an intersection distal to said penetrator.

26. The surgical device according to claim 25, wherein said first blade edge, said second blade edge, and further blade edge intersect at a cutting tip of said cutting blade.

27. The surgical device according to claim 19, wherein the penetrator is removably insertable into the handle.

28. A surgical device according to claim 27, which comprises:
a locking system for locking and unlocking the guard in position so as to selectably expose said cutting blade during cutting of the tissue and to progressively cover the end of the cutting blade after a most distal point of the cutting blade has substantially passed through a layer of the tissue.

29. A surgical device according to claim 19, which comprises:
a locking system for locking and unlocking the guard in position so as to selectably expose said cutting blade during cutting of the tissue and to progressively cover the cutting tip of the cutting blade after a most distal point of the cutting tip has substantially passed through a layer of the tissue.

30. A surgical device according to claim 29, which comprises:
a locking system for locking and unlocking the guard in position so as to selectably expose said cutting blade during cutting of the tissue and to progressively cover the end of the cutting blade after a most distal point of the cutting blade has substantially passed through a layer of the tissue.

31. A surgical device, comprising:
a penetrator having a main axis and being removably attachable to a handle for being gripped;
at least one cutting blade located at a distal end of said penetrator and being connected thereto; and
a guard movable with respect to said at least one cutting blade and being configured to selectively expose said at least one cutting blade wherein said guard has an apex such that an angle subscribed in the apex of the guard is smaller than an angle subscribed by said at least one cutting blade for progressively covering said at least one cutting blade during deployment of the penetrator.

32. A surgical device according to claim 31, wherein said cutting blade has one of a substantially dull tip and a substantially rounded tip.

33. A surgical device according to claim 31, wherein the penetrator is removably insertable into the handle.

34. A surgical device according to claim 33, which comprises:
a locking system for locking and unlocking the guard in position so as to selectably expose said cutting blade during cutting of the tissue and to progressively cover the cutting tip of the cutting blade after a most distal point of the cutting tip has substantially passed through a layer of the tissue.

35. A surgical device according to claim 31, which comprises:
a locking system for locking and unlocking the guard in position so as to selectably expose said cutting blade during cutting of the tissue and to progressively cover the cutting tip of the cutting blade after a most distal point of the cutting tip has substantially passed through a layer of the tissue.

36. A surgical device, comprising:
a handle configured to be gripped;
a penetrator having a main axis and attached to said handle;
at least one cutting blade located at a distal end of said penetrator and having a cutting tip;
a guard configured to slidably cover and uncover said cutting tip, said guard being movable with respect to said at least one cutting tip and being configured to selectively expose said cutting tip; and a locking mechanism configured to hinder an accidental uncovering of said cutting tip by said guard wherein said guard has an apex such that an angle subscribed in the apex of the guard is smaller than an angle subscribed by said blade for progressively covering said blade during deployment of the penetrator.

37. A surgical device according to claim 36, wherein said cutting tip comprises one of a dull tip and a substantially rounded tip.

38. The surgical device according to claim 36, wherein the penetrator is removably insertable into the handle.

39. A surgical device according to claim 38, which comprises:

a locking system for locking and unlocking the guard in position so as to selectably expose said cutting blade during cutting of the tissue and to progressively cover the cutting tip of the cutting blade after a most distal point of the cutting tip has substantially passed through a layer of the tissue.

40. A surgical device, comprising:

a penetrator having a main axis and attachable to a handle for being gripped;

at least one cutting blade located at a distal end of said penetrator; wherein said handle includes:

a guard for slidably covering and uncovering said at least one cutting blade, said guard being moveable with respect to said tissue expander;

at least one side horn configured to facilitate pushing, pulling, rotation, and tilting of said surgical device wherein said guard has an apex such that an angle subscribed in the apex of the guard is smaller than an angle subscribed by said at least one cutting blade for progressively covering said at least one cutting blade during deployment of the penetrator.

41. A surgical device according to claim 40, wherein said cutting blade has one of a dull tip and a substantially rounded tip.

42. The surgical device comprising:

means mountable on means for gripping said surgical device for passing an object of interest into a hole in a tissue member;

means mounted on said means for passing object into the hole in the tissue member for cutting the hole for insertion of said means for passing an object into the hole in the tissue member, said means for cutting the hole being movable with respect to said means for expanding tissue; and means for halting said means for cutting wherein said means for halting comprises means for guarding said means for cutting, said means for guarding said means for cutting being movable with respect to said means for expanding the tissue member wherein said means for guarding said means for cutting has an apex such that an angle subscribed in the apex of the means for guarding is smaller than an angle subscribed by said means for cutting for progressively covering said means for cutting during deployment of said means for expanding the tissue member.

43. The surgical device according to claim 42, wherein said cutting blade has one of a dull tip means and a substantially rounded tip means.

44. A surgical device, comprising:

penetrator means having a main axis and being attachable to a handle;

means for cutting tissue located at a distal end of said penetrator means;

guard means movable with respect to said tissue expander means and configured to selectively expose said means for cutting tissue wherein said means for guarding said means for cutting tissue has an apex such that an angle subscribed at the apex of the means for guarding is smaller than an angle subscribed by said means for cutting tissue for progressively covering said means for cutting tissue during cutting of the tissue.

45. A surgical device as claimed in claim 44, wherein said means for cutting tissue comprises one of a dull tip means and a substantially rounded tip means.

* * * * *

UNITED STATES PATENT AND TRADEMARK OFFICE
CERTIFICATE OF CORRECTION

PATENT NO. : 6,716,201 B2 Page 1 of 1
DATED : April 6, 2004
INVENTOR(S) : Ernesto E. Blanco It is certified that error appears in the above-identified patent and that said Letters Patent is hereby corrected as shown below:

Column 13,
Line 31, after "guard edge", insert -- angle --.

Signed and Sealed this

Third Day of May, 2005

JON W. DUDAS
*Director of the United States Patent and Trademark Office*